(12) United States Patent
Wormington et al.

(10) Patent No.: US 9,829,448 B2
(45) Date of Patent: Nov. 28, 2017

(54) MEASUREMENT OF SMALL FEATURES USING XRF

(71) Applicant: JORDAN VALLEY SEMICONDUCTORS LTD., Migdal HaEmek (IL)

(72) Inventors: Matthew Wormington, Littleton, CO (US); Isaac Mazor, Haifa (IL); Alex Tokar, Haifa (IL); Alex Dikopoltsev, Haifa (IL)

(73) Assignee: BRUKER JV ISRAEL LTD., Migdal Haemek (IL)

( * ) Notice: Subject to any disclaimer, the term of this patent is extended or adjusted under 35 U.S.C. 154(b) by 259 days.

(21) Appl. No.: 14/922,220

(22) Filed: Oct. 26, 2015

(65) Prior Publication Data

US 2016/0123909 A1    May 5, 2016

Related U.S. Application Data

(60) Provisional application No. 62/072,471, filed on Oct. 30, 2014.

(51) Int. Cl.
*G01N 23/223*   (2006.01)
*G01B 15/02*    (2006.01)

(52) U.S. Cl.
CPC .......... *G01N 23/223* (2013.01); *G01B 15/02* (2013.01); *G01N 2223/303* (2013.01)

(58) Field of Classification Search
CPC ............. G01B 15/02; G01N 2223/303; G01N 23/223; G01N 2223/076; G01N 23/2252;
(Continued)

(56) References Cited

U.S. PATENT DOCUMENTS

| 2,711,480 A | 6/1955 | Friedman |
| 3,256,431 A | 6/1966 | Frazer |

(Continued)

FOREIGN PATENT DOCUMENTS

| JP | 6186344 A  | 7/1994 |
| JP | 06273146 A | 9/1994 |

(Continued)

OTHER PUBLICATIONS

Singer, "Copper CMP: Taking aim at Dishing", Semiconductor International (www.reed-electronics.com/semiconductor/), 4 pages, Oct. 1, 2004.

(Continued)

*Primary Examiner* — Irakli Kiknadze
(74) *Attorney, Agent, or Firm* — D. Kligler IP Services Ltd.

(57) ABSTRACT

A method for X-ray measurement includes, in a calibration phase, scanning a first X-ray beam, having a first beam profile, across a feature of interest on a calibration sample and measuring first X-ray fluorescence (XRF) emitted from the feature and from background areas of the calibration sample surrounding the feature. Responsively to the first XRF and the first beam profile, a relative emission factor is computed. In a test phase, a second X-ray beam, having a second beam profile, different from the first beam profile, is directed to impinge on the feature of interest on a test sample and second XRF emitted from the test sample is measured in response to the second X-ray beam. A property of the feature of interest on the test sample is computed by applying the relative emission factor together with the second beam profile to the measured second XRF.

20 Claims, 7 Drawing Sheets

(58) Field of Classification Search
CPC ........... G01N 21/274; G01N 2223/616; G01N 2021/6419; G01N 2021/6421; G01N 2021/6439; G01N 2021/6441; G01N 2021/6463; G01N 2021/6482; G01N 21/6428; G01N 21/645; G01N 21/6452; B60K 2350/1024; B60K 2350/1028; B60K 35/00; B60K 37/06; B60R 11/0235; B60R 1/12; B60R 2001/1215; B60R 2001/1253; B60R 2011/0082; G01C 21/265; A61B 6/032; A61B 6/027; A61B 6/488; A61B 6/463; A61B 6/469; A61B 6/481; A61B 6/507; A61B 6/583; A61B 6/0457; A61B 6/4021; A61B 6/4085; A61B 6/5205; A61B 6/5258; A61B 6/5282; G06T 11/006; G06T 2211/421; G06T 11/005

See application file for complete search history.

(56) References Cited

U.S. PATENT DOCUMENTS

| | | |
|---|---|---|
| 3,581,087 A | 5/1971 | Brinkerhoff |
| 3,754,138 A | 8/1973 | Kurstedt et al. |
| 3,919,548 A | 11/1975 | Porter |
| 3,980,568 A | 9/1976 | Pitchford et al. |
| 3,984,680 A | 10/1976 | Smith |
| 4,048,496 A | 9/1977 | Albert |
| 4,085,329 A | 4/1978 | McCoy et al. |
| 4,169,228 A | 9/1979 | Briska et al. |
| 4,377,869 A | 3/1983 | Venalainen et al. |
| 4,446,568 A | 5/1984 | Williams et al. |
| 4,551,905 A | 11/1985 | Chao et al. |
| 4,590,603 A | 5/1986 | Relihan et al. |
| 4,710,259 A | 12/1987 | Howe et al. |
| 4,718,075 A | 1/1988 | Horn |
| 4,725,963 A | 2/1988 | Taylor et al. |
| 4,847,882 A | 7/1989 | Knoth et al. |
| 4,852,135 A | 7/1989 | Anisovich et al. |
| 4,916,720 A | 4/1990 | Yamamoto et al. |
| 4,989,226 A | 1/1991 | Woodbury et al. |
| 5,151,588 A | 9/1992 | Kiri et al. |
| 5,365,563 A | 11/1994 | Kira et al. |
| 5,385,867 A | 1/1995 | Ueda et al. |
| 5,425,066 A | 6/1995 | Takahashi et al. |
| 5,481,109 A | 1/1996 | Ninomiya et al. |
| 5,497,008 A | 3/1996 | Kumakhov |
| 5,574,284 A | 11/1996 | Farr |
| 5,619,548 A | 4/1997 | Koppel |
| 5,740,226 A | 4/1998 | Komiya et al. |
| 5,742,658 A | 4/1998 | Tiffin et al. |
| 5,778,039 A | 7/1998 | Hossain et al. |
| 5,877,498 A | 3/1999 | Sugimoto et al. |
| 5,893,758 A | 4/1999 | Sandhu et al. |
| 5,900,645 A | 5/1999 | Yamada |
| 5,909,276 A | 6/1999 | Kinney et al. |
| 5,923,720 A | 7/1999 | Barton et al. |
| 5,937,026 A | 8/1999 | Satoh |
| 5,937,027 A | 8/1999 | Thevenin et al. |
| 5,949,847 A | 9/1999 | Terada et al. |
| 5,963,329 A | 10/1999 | Conrad et al. |
| 6,001,736 A | 12/1999 | Kondo et al. |
| 6,040,095 A | 3/2000 | Enichen et al. |
| 6,041,095 A | 3/2000 | Yokhin |
| 6,041,098 A | 3/2000 | Touryanski et al. |
| 6,108,398 A | 8/2000 | Mazor et al. |
| 6,173,036 B1 | 1/2001 | Hossain et al. |
| 6,192,103 B1 | 2/2001 | Wormington et al. |
| 6,226,347 B1 | 5/2001 | Golenhofen |
| 6,226,349 B1 | 5/2001 | Schuster et al. |
| 6,266,389 B1 | 7/2001 | Murayama et al. |
| 6,345,086 B1 | 2/2002 | Ferranolino et al. |
| 6,351,516 B1 | 2/2002 | Mazor et al. |
| 6,381,303 B1 | 4/2002 | Vu et al. |
| 6,389,102 B2 | 5/2002 | Mazor et al. |
| 6,453,002 B1 | 9/2002 | Mazor et al. |
| 6,453,006 B1 | 9/2002 | Koppel et al. |
| 6,507,634 B1 | 1/2003 | Koppel et al. |
| 6,512,814 B2 | 1/2003 | Yokhin et al. |
| 6,556,652 B1 | 4/2003 | Mazor et al. |
| 6,639,968 B2 | 10/2003 | Yokhin et al. |
| 6,643,354 B2 | 11/2003 | Koppel et al. |
| 6,680,996 B2 | 1/2004 | Yokhin et al. |
| 6,704,661 B1 | 3/2004 | Opsal et al. |
| 6,711,232 B1 | 3/2004 | Janik |
| 6,744,850 B2 | 6/2004 | Fanton et al. |
| 6,744,950 B2 | 6/2004 | Aleksoff |
| 6,750,952 B2 | 6/2004 | Grodnensky et al. |
| 6,754,304 B1 | 6/2004 | Kumakhov |
| 6,754,305 B1 | 6/2004 | Rosencwaig et al. |
| 6,771,735 B2 | 8/2004 | Janik et al. |
| 6,810,105 B2 | 10/2004 | Nasser-Ghodsi et al. |
| 6,823,043 B2 | 11/2004 | Fewster et al. |
| 6,879,051 B1 | 4/2005 | Singh et al. |
| 6,890,575 B2 | 5/2005 | Beauregard et al. |
| 6,891,627 B1 | 5/2005 | Levy et al. |
| 6,895,075 B2 | 5/2005 | Yokhin et al. |
| 6,947,520 B2 | 9/2005 | Yokhin et al. |
| 6,977,986 B1 | 12/2005 | Beanland et al. |
| 7,023,954 B2 | 4/2006 | Rafaeli et al. |
| 7,062,013 B2 | 6/2006 | Berman et al. |
| 7,068,753 B2 | 6/2006 | Berman et al. |
| 7,071,007 B2 | 7/2006 | Tseng et al. |
| 7,103,142 B1 | 9/2006 | Agnihotry et al. |
| 7,110,491 B2 | 9/2006 | Mazor et al. |
| 7,120,228 B2 | 10/2006 | Yokhin et al. |
| 7,130,376 B2 | 10/2006 | Berman et al. |
| 7,183,547 B2 | 2/2007 | Yun et al. |
| 7,245,695 B2 | 7/2007 | Mazor et al. |
| 7,551,719 B2 | 6/2009 | Yokhin et al. |
| 7,600,916 B2 | 10/2009 | Yokhin et al. |
| 7,649,978 B2 | 1/2010 | Mazor et al. |
| 7,653,174 B2 | 1/2010 | Mazor et al. |
| 7,804,934 B2 | 9/2010 | Agnihotri et al. |
| 7,968,444 B2 | 6/2011 | Luo et al. |
| 2001/0028699 A1 | 10/2001 | Iwasaki |
| 2001/0043668 A1 | 11/2001 | Hayashi et al. |
| 2002/0097837 A1 | 7/2002 | Fanton et al. |
| 2002/0110218 A1 | 8/2002 | Koppel et al. |
| 2003/0012337 A1 | 1/2003 | Fewster et al. |
| 2003/0128809 A1 | 7/2003 | Umezawa et al. |
| 2003/0157559 A1 | 8/2003 | Omote et al. |
| 2004/0052330 A1 | 3/2004 | Koppel et al. |
| 2004/0109531 A1 | 6/2004 | Yokhin et al. |
| 2004/0131151 A1 | 7/2004 | Berman et al. |
| 2004/0156474 A1 | 8/2004 | Yokhin et al. |
| 2004/0218717 A1 | 11/2004 | Koppel et al. |
| 2004/0267490 A1 | 12/2004 | Opsal et al. |
| 2005/0282300 A1 | 12/2005 | Yun et al. |
| 2006/0062350 A1 | 3/2006 | Yokhin et al. |
| 2006/0227931 A1 | 10/2006 | Mazor et al. |
| 2006/0274886 A1 | 12/2006 | Mazor et al. |
| 2008/0021665 A1 | 1/2008 | Vaughnn |
| 2008/0049895 A1 | 2/2008 | Agnihotri et al. |
| 2008/0095309 A1 | 4/2008 | Puusaari et al. |
| 2008/0159475 A1 | 7/2008 | Mazor et al. |
| 2009/0074137 A1* | 3/2009 | Agnihotri ............... G01B 15/02 378/50 |
| 2009/0262889 A1* | 10/2009 | Dugas .................. G01N 23/223 378/45 |
| 2010/0189215 A1* | 7/2010 | Grodzins ............. G01N 23/223 378/45 |
| 2013/0089178 A1 | 4/2013 | Mazor et al. |
| 2013/0202084 A1* | 8/2013 | Piorek .................. G01N 23/223 378/45 |
| 2014/0286473 A1 | 9/2014 | Tokar et al. |
| 2015/0330921 A1 | 11/2015 | Mazor et al. |

FOREIGN PATENT DOCUMENTS

| | | |
|---|---|---|
| JP | 2006283585 A | 10/1994 |
| JP | 07019844 A | 1/1995 |

(56) References Cited

FOREIGN PATENT DOCUMENTS

| | | | |
|---|---|---|---|
| JP | 7128259 A | 5/1995 | |
| JP | 09308339 A | 12/1997 | |
| JP | 10048398 A | 2/1998 | |
| JP | 10318949 A | 12/1998 | |
| JP | 2004003959 A | 1/2004 | |
| JP | 2004151004 A | 5/2004 | |
| WO | 92/08235 A1 | 5/1992 | |

OTHER PUBLICATIONS

Reed Electronics Group, Semiconductor International, "Webcast Equipment Auction" (www.reed-electronics.com/semiconductor/), 2 pages, Dec. 15, 2005.
Dane et al., "Application of Genetic Algorithms for Characterization of Thin Layered Materials by Glancing Incidence X-Ray Reflectometry", Physica B 253, pp. 254-268, Feb. 26, 1998.
Kozaczek et al., "X-Ray Diffraction Metrology for 200 mm Process Qualification and Stability Assessment", Advanced Metallization Conference, Montreal, Canada, 6 pages, Oct. 8-11, 2001.
Powell et al., "X-Ray Diffraction and Reflectivity Characterization of SiGe Superlattice Structures", Semiconductor Science and Technology Journal, vol. 7, No. 5, pp. 627-631, United Kingdom, 1992.
Neissendorfer et al., "The Energy-Dispersive Reflectometer / Diffractometer at BESSY-I", Measurement Science and Technology Journal, vol. 10, No. 5, pp. 354-361, year 1999.
Ulyanenkov, "Introduction to High Resolution X-Ray Diffraction", Workshop on X-Ray Characterization to Thin Layers, 50 pages, Uckley, May 21-23, 2003.
Huang et al., "Characterization of Single and Multiple-Layer Films by X-Ray Reflectometry", Advances in X-Ray Analysis, vol. 35, pp. 137-142, New York, USA, 1992.
EX-6500 Advanced EDXRF Spectrometer Manufactures by Jordan Valley Semiconductors, 2 pages, year 2000.
Lengeler, "X-Ray Reflection, A New Tool for Investigating Layered Structures and Interfaces", Advances in X-Ray.Analysis, Plenum Press, vol. 35, pp. 127-135, New York, USA, 1992.
Lankosz et al., "Research in Quantitative X-Ray Fluorescence Microanalysis of Patterned This Films", Advances in X-Ray Analysis, vol. 43, pp. 497-503, year 1999.
Parrill et al., "GISAXS—Glancing Incidence Small Angle X-Ray Scattering", Journal de Physique IV, supplement to Journal de Physique I, vol. 3, pp. 411-417, Dec. 1993.
Bowen et al., "X-Ray Metrology by Diffraction and Reflectivity", 2000 International Conference on Characterization and Metrology for ULSI Technology, NIST, Gaithersburg, Maryland, USA, pp. 570-579, Jun. 26-29, 2000.
Naudon et al., "New Apparatus for Grazing X-Ray Reflectometry in the Angle-Resolved Dispersive Mode", Journal of Applied Crystallography, vol. 22, pp. 460-464, year 1989.
X-Ray Optical Systems, Inc., "Monolithic Polycapillary Lens Information", Albany, USA, 1 page, Dec. 29, 1998.
Markowicz et al., "Quantification in XRF Analysis of Intermediate-Thickness Samples", Handbook of X-Ray Spectrometry, 2nd edition, chapter 6, pp. 408-431, Antwerp, Belgium, CRC Press 2001.
U.S. Appl. No. 11/018,352, Office Action dated Feb. 8, 2006.
U.S. Appl. No. 11/889,337, Office Action dated Jul. 24, 2008.
U.S. Appl. No. 11/018,352, Office Action dated Oct. 24, 2005.
U.S. Appl. No. 11/487,433, Office Action dated May 29, 2008.
U.S. Appl. No. 12/003,215, Office Action dated Apr. 1, 2009.
U.S. Appl. No. 11/103,071, Office Action dated Oct. 5, 2006.
U.S. Appl. No. 09/028,588, Office Action dated Jun. 4, 1999.
Jones et al., "Small Angle X-Ray Scattering for sub-100 nm Pattern Characterization", Journal of Applied Physics, vol. 83, No. 19, pp. 4059-4061, Nov. 10, 2003.
Hu et al., "Small Angle X-Ray Scattering Metrology for Sidewall Angle and Cross Section of Nanometer Scale Line Gratings", Journal of Applied Physics, vol. 96, No. 4, pp. 1983-1987, Aug. 15, 2004.
Wu et al., "Small Angle Neutron Scattering Measurements of Nanoscale Lithographic Features", Polymer Preprints, vol. 42, No. 1, pp. 265-266, year 2001.
Kojima et al., "Structural Characterization of Thin Films by X-Ray Reflectivity", Rigaku Journal, vol. 16, No. 2, pp. 31-41, year 1999.
X-Ray Optical Systems, Inc., "Micro X-Ray Fluorescence with Focusing Polycapillary Optics", Application Note 102, 2 pages, USA, Jun. 12, 2002.
Guerault, "Specular Reflectivity and Off-Specular Scattering: Tools for Roughness Investigation", Institute Voor Kern—en Stralingsfysica, 15 pages, Dec. 15, 2000.
Wiener et al., "Characterization of Titanium Nitride Layers by Grazing—Emission X-Ray Fluorescence Spectrometry", Applied Surface Science, vol. 125, pp. 129-136, Elsevier Science B.V., year 1999.
Hayashi et al., "Refracted X-Rays Propagating Near the Surface Under Grazing Incidence Condition", Spectrochimica Acta, Part B 54, pp. 227-230, year 1999.
Di-Fonzo et al., "Non-Destructive Determination of Local Strain with 100 - Nanometre Spatial Resolution", Letters to Nature, vol. 403, pp. 638-640, Feb. 10, 2000.
Agnihotri, U.S. Appl. No. 11/610,174, "Accurate Measurement of Layer Dimensions using XRF", filed Dec. 13, 2006 (abandoned).
Japan Patent Application 2007-340602, Office Action dated Apr. 24, 2012.
Leng et al., "Simultaneous Measurement of Six Layers in a Silicon on Insulator Film Stack using Spectrophotometry and Beam Profile Reflectometry", Journal of Applied Physics, vol. 81, No. 8, pp. 3570-3578, Apr. 15, 1997.
Boer, "Calculation of X-Ray Fluorescence Intensities from Bulk and Multilayer Samples", X-Ray Spectrometry, vol. 19, pp. 145-154, 1990.
Mantler, "X-ray fluorescence analysis of multiple-layer films", Analytica chimica acta, vol. 188, pp. 25-35, 1986.
Patterson, "Transforming mobile electronics with copper pillar interconnect", Advancing microelectronics, vol. 39, No. 3, pp. 18-24, May/Jun. 2012.
Beckhoff et al, "Handbook of Practical X-Ray Fluorescence Analysis", Springer-Verlag, Berlin, Heidelberg , pp. 1-30, 2006.
U.S. Appl. No. 13/647,408 Official Action dated Jul. 25, 2014.
Boer et al., "How Accurate is the Fundamental Parameter approach? XRF Analysis of Bulk and Multilayer Samples", X-Ray Spectrometry, vol. 22, pp. 33-38, 1993.
U.S. Appl. No. 13/647,408 Office Action dated Oct. 30, 2014.
U.S. Appl. No. 13/647,408 Office Action dated Jul. 8, 2015.
U.S. Appl. No. 14/222,635 Office Action dated Dec. 7, 2015.
U.S. Appl. No. 14/708,323 Office Action dated Aug. 16, 2016.

* cited by examiner

MEASUREMENT OF SMALL FEATURES USING XRF

CROSS-REFERENCE TO RELATED APPLICATIONS

This application claims the benefit of U.S. Provisional Patent Application 62/072,471, filed Oct. 30, 2014, which is incorporated herein by reference.

FIELD OF THE INVENTION

The present invention relates generally to X-ray systems and methods, and specifically to measurement of small features using X-ray fluorescence.

BACKGROUND

X-ray fluorescence (XRF) measurement, and specifically X-ray microfluorescence (i.e., X-ray fluorescence using focused excitation beams of small diameter, typically less than 100 μm), is commonly used in testing semiconductor wafers. XRF itself is a well-known technique for determining the elemental composition and other properties, such as thickness, of a sample. XRF analyzers generally include an X-ray source, which irradiates the sample with sufficient energy to excite X-ray fluorescence from the elements of interest within the sample, and an X-ray detector, for detecting the X-ray fluorescence emitted by the sample in response to the irradiation. Each element in the sample emits X-ray fluorescence at discrete energies that are characteristic of the element. The detected X-ray fluorescence is analyzed to find the energies or, equivalently, the wavelengths of the detected photons and the number of emitted photons (intensity) as a function of energy or wavelength, and the qualitative and/or quantitative composition, thickness and/or other properties of the sample are determined based on this analysis.

U.S. Pat. No. 6,108,398, for example, whose disclosure is incorporated herein by reference, describes an XRF analyzer and a method for analyzing a sample. The analyzer includes an X-ray beam generator, which generates an X-ray beam incident at a spot on the sample and creates a plurality of fluorescent X-ray photons. An array of semiconductor detectors is arranged around the spot so as to capture the fluorescent X-ray photons. The analyzer produces electrical pulses suitable for analysis of the sample.

The use of X-ray microfluorescence for testing semiconductor wafers is described in U.S. Pat. No. 6,351,516, whose disclosure is incorporated herein by reference. This patent describes a non-destructive method for testing the deposition and/or the removal of a material within a recess on the surface of a sample. An excitation beam is directed onto a region of the sample in a vicinity of the recess, and an intensity of X-ray fluorescence emitted from the region is measured. A quantity of the material that is deposited within the recess is determined responsively to the measured intensity.

U.S. Pat. No. 7,653,174, whose disclosure is incorporated herein by reference, describes methods for inspection of small features using X-ray fluorescence. These methods are based on measuring the intensity of X-ray emission from a sample at multiple different locations of an irradiating X-ray beam relative to a target feature on the sample. The corresponding intensity measurements are processed in order to give an adjusted value of the emission, which is more accurately indicative of characteristics (such as thickness) of the feature.

U.S. Patent Application Publication 2013/0089178, whose disclosure is incorporated herein by reference, describes a method for inspection of a feature formed on a semiconductor wafer, which includes a volume containing a first material and a cap made of a second material, different from the first material, that is formed over the volume. The feature is irradiated with a focused beam, and one or more detectors positioned at different angles relative to the feature are used to detect X-ray fluorescent photons that are emitted by the first material in response to the irradiating beam and pass through the cap before striking the detectors. Signals output by the one or more detectors at the different angles in response to the detected photons are processed in order to assess a quality of the cap.

U.S. Patent Application Publication 2014/0286473, whose disclosure is incorporated herein by reference, describes a method for inspection that includes capturing an optical image of one or more features on a surface of a sample and irradiating an area of the sample containing at least one of the features with an X-ray beam. An intensity of X-ray fluorescence emitted from the sample in response to the irradiating X-ray beam is measured. The optical image is processed so as to extract geometrical parameters of the at least one of the features and to compute a correction factor responsively to the geometrical parameters. The correction factor is applied to the measured intensity in order to derive a property of the at least one of the features.

SUMMARY

Embodiments of the present invention that are described hereinbelow provide improved methods and apparatus for inspection of small structures using X-ray fluorescence.

There is therefore provided, in accordance with an embodiment of the invention, a method for X-ray measurement, which includes, in a calibration phase, scanning a first X-ray beam, having a first beam profile, across a feature of interest on a calibration sample and measuring first X-ray fluorescence (XRF) emitted, in response to the first X-ray beam, from the feature and from background areas of the calibration sample surrounding the feature. Responsively to the first XRF and the first beam profile, a relative emission factor, indicative of a relation of XRF emission intensities between the feature and the background areas surrounding the feature, is computed. In a test phase, a second X-ray beam, having a second beam profile, different from the first beam profile, is directed to impinge on the feature of interest on a test sample and second XRF emitted from the test sample is measured in response to the second X-ray beam. A property of the feature of interest on the test sample is measured by applying the relative emission factor together with the second beam profile to the measured second XRF.

Typically, the computed property is selected from a group of properties consisting of a composition and a thickness of the feature. In a disclosed embodiment, computing the property includes computing, based upon the relative emission factor and the second beam profile, an environmental correction factor, calculating a corrected intensity of the second XRF by scaling a measured intensity of the second XRF by the environmental correction factor, and deriving the computed composition or thickness from the corrected intensity. The environmental correction factor depends upon and compensates for a fraction of the second X-ray beam that is incident on the background areas surrounding the feature of interest on the test sample.

In some embodiments, computing the relative emission factor includes measuring the first XRF and computing different, respective relative emission factors for a plurality of different elements in the feature of interest, at different, respective XRF energies, and computing the property includes selecting one or more of the respective relative emission factors to apply depending upon an energy of the measured second XRF.

In some embodiments, the method includes, in the calibration phase, measuring the first beam profile. Typically, measuring the first beam profile includes measuring a width of the first beam at a plurality of different energies of the first X-ray beam, and finding an energy-dependence of the width, and computing the relative emission factor includes estimating, based on the energy-dependence, the width of the first beam at a specified energy, and applying the estimated width in finding the relative emission factor. In a disclosed embodiment, measuring the first beam profile includes, at each of the different energies, scanning the first X-ray beam across an edge of a target, and measuring an intensity of the XRF from the target while scanning the first X-ray beam.

Additionally or alternatively, the method includes, in the test phase, measuring the second beam profile, wherein computing the property includes applying the measured second beam profile, together with the relative emission factor, in computing the property.

In a disclosed embodiment, the calibration and test samples include semiconductor wafers, and the feature of interest includes a metal pad formed in a predefined location on each of the semiconductor wafers, while the background areas contain other structures formed on the semiconductor wafers around the predefined location.

There is also provided, in accordance with an embodiment of the invention, apparatus for X-ray measurement, including an X-ray beam source, which is configured to direct an X-ray beam to impinge on a sample, and an X-ray detector, which is configured to sense X-ray fluorescence (XRF) emitted from the sample in response to the X-ray beam. A motion assembly is configured to cause the X-ray beam to scan across the sample. A processor is configured to control the X-ray beam source and the motion assembly and to receive signals from the X-ray detector in response to the emitted XRF in a calibration phase and in a test phase. In the calibration phase, the motion assembly scans a first X-ray beam, having a first beam profile, across a feature of interest on a calibration sample and the processor measures first XRF emitted, in response to the first X-ray beam, from the feature and from background areas of the calibration sample surrounding the feature and computes, responsively to the first XRF and the first beam profile, a relative emission factor indicative of a relation of XRF emission intensities between the feature and the background areas surrounding the feature. In the test phase, the X-ray source directs a second X-ray beam, having a second beam profile, different from the first beam profile, to impinge on the feature of interest on a test sample, and the processor measures second XRF emitted from the test sample in response to the second X-ray beam and computes a property of the feature of interest on the test sample by applying the relative emission factor together with the second beam profile to the measured second XRF.

The present invention will be more fully understood from the following detailed description of the embodiments thereof, taken together with the drawings in which:

DETAILED DESCRIPTION OF EMBODIMENTS

Figure 1:
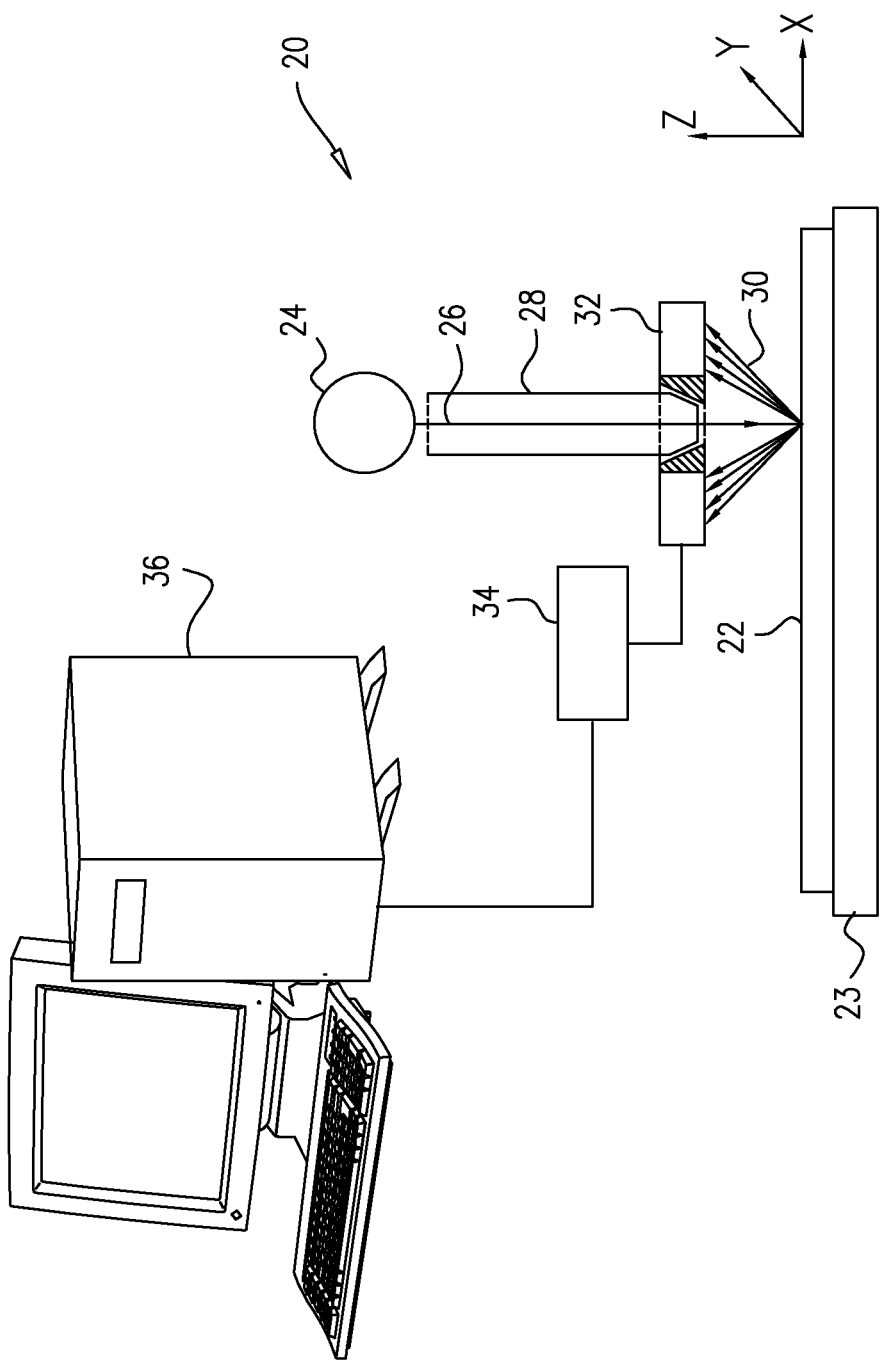
FIG. 1 is a schematic illustration of a system for X-ray microfluorescence measurement, in accordance with an embodiment of the present invention.

Embodiments of the present invention that are described herein are directed to measurement of properties, such as composition and thickness, of small features using X-ray microfluorescence. In the context of the present patent application, "small" refers to features of a sample, such as regions of an integrated circuit on a semiconductor wafer, whose dimensions are comparable to or less than the diameter of the X-ray spot on the surface of the sample, which is typically less than 50 μm. In an integrated circuit device, the values of these parameters can be critical to the performance, reliability and yield of the device, but they are otherwise difficult or impossible to measure accurately and non-destructively. The methods of micro-XRF that are described hereinbelow are directed particularly to evaluation of the properties of pads that are formed on a wafer for purposes of characterization or metrology. The principles of the present invention, however, may similarly be applied in inspection of small features of other sorts, both on semiconductor wafers and on other sorts of samples.

When an X-ray beam is focused onto a pad of interest (POI), it is ideally desirable, for purposes of measurement accuracy, that the X-ray beam be centered on the pad and that all incident intensity impinges only on that pad. In practice, however, such conditions cannot be achieved if the X-ray beam size on the sample is comparable to the pad being measured. In this case, the beam tends to "spill off" the pads. In other words, only a fraction of the incident X-ray intensity actually excites fluorescence of the pad of interest, while the remainder of the beam excites background fluorescence from neighboring areas and features. It is necessary that the fluorescence intensity be corrected in order to give an accurate measurement of the properties of the pad of interest.

The correction that is needed depends both on the spatial distribution of the intensity (profile) of the X-ray beam that is used to excite the XRF from the POI and on the emission of the surrounding areas (also referred to herein as "background areas") in the XRF line or lines of interest. For a given X-ray beam profile and POI, the relative contribution of the background areas to the XRF emission can be calibrated in advance and used to correct the measurements made in a given testing "recipe." As soon as the beam profile changes, however—due to changing the X-ray tube or adjustment of the X-ray optics, for example—the contribution of the background to the XRF emission, relative to the POI, will change, and the calibration factors derived previously will be inaccurate.

Embodiments of the present invention that are described herein address this problem by providing calibration techniques that make it possible to continue using a test recipe even when the beam profile has changed, without having to repeat the calibration phase of the recipe. In the calibration (recipe setup) phase, an X-ray beam is scanned across a feature of interest, such as a POI, on a calibration sample that is representative of the test samples that are to be evaluated subsequently; and the XRF emitted in response to the X-ray beam, from the feature and from background areas of the calibration sample surrounding the feature, is measured. Based on the XRF and the known profile of the X-ray beam, a processor computes a relative emission factor, referred to hereinbelow as a "thickness factor," which is indicative of the relation of XRF emission intensities between the feature and background areas but is independent of the beam geometry.

The parameters that are found in the calibration phase typically apply to a range of different X-ray beam energies and XRF emission lines. The X-ray beam profile typically varies as a function of the X-ray beam energy, while the relative emission factor varies for different XRF emission lines, depending upon the elements in a given POI and background areas that give rise to the emission. In the calibration phase, in order to compensate for these variations, the dependence of beam profile on beam energy may also be measured, and multiple relative emission factors may be computed for different elements in the POI. The range and choices of beam energies and XRF emission lines may vary from recipe to recipe.

In the test phase, following the calibration phase, the recipe is typically applied to multiple test samples, such as semiconductor wafers in stages of production. The X-ray beam is directed to impinge on the feature of interest on a test sample, and the emitted XRF is again measured. As noted earlier, the X-ray beam that is used in the test phase may have a beam profile that is different from the beam used in the calibration phase. The beam profile may be re-measured at this stage or at any other time when re-measurement is considered desirable (for example, following system maintenance), but without the necessity of repeating the entire recipe calibration procedure. Using the known beam profile and the appropriate relative emission factors found in the calibration phase, a processor corrects the measured XRF intensity and thus accurately computes a property of the feature of interest on the test sample, notwithstanding the change in the beam profile.

In a disclosed embodiment, as explained further hereinbelow, the processor finds the corrected XRF intensity by scaling the measured XRF intensity by an environmental correction factor (ECF). This factor compensates for the fraction of the X-ray beam that is "lost" to the background areas surrounding the feature of interest on the test sample, as well as for the relative intensity of XRF emission from these areas. The ECF thus depends on both the profile of the X-ray beam that is used to excite the XRF and the element whose fluorescence is measured, and it is therefore computed in each application of the recipe using the current, known beam profile and the relative emission factor appropriate to the element in question. This approach affords a high degree of both accuracy and flexibility in measurements made over many test samples using a given recipe, including implementation of the same recipe on different testing tools, while avoiding the need for recipe recalibration.

FIG. 1 is a schematic illustration of an X-ray microfluorescence analysis system 20, in accordance with an embodiment of the present invention. Aspects of system 20 are described in detail in the above-mentioned U.S. Pat. No. 6,108,398. System 20 is arranged to examine a semiconductor wafer 22 (or another sample), in order to measure properties of features formed on the wafer during the fabrication process, using methods described hereinbelow. For example, system 20 may measure and analyze the properties of a pad of interest (POI), including composition and thickness, in order to verify proper operation of a fabrication process that is applied in forming both the POI and functional features on wafer 22.

System 20 comprises an excitation source, such as an X-ray tube 24, driven by a high-voltage power supply, as is known in the art. X-ray tube 24 emits an X-ray beam 26, having a suitable energy range and flux, into X-ray optics 28. The optics may comprise a polycapillary array, for example. Optics 28 focus the X-ray beam onto a small region, typically a spot on the order of 5-50 μm in diameter (although larger and, possibly, smaller spot sizes may be used), on the surface of wafer 22. The irradiated region emits fluorescent X-rays 30, which are captured by an array of detectors 32, which are arranged around the irradiated region and may be angled toward it. The detectors may comprise any suitable type of X-ray detectors, such as Si(Li) (lithium-drifted silicon) detectors or silicon drift detectors (SDDs), which generate pulses whose amplitude is proportional to the energy of the incident X-ray photons. In response to the captured photons, detectors 32 generate electrical signals, which are conveyed to a signal analyzer 34.

Alternatively, other types of X-ray fluorescence analyzers known in the art, comprising any suitable excitation source, power source, focusing optics and detection system, may be used in implementing the methods described herein. For example, a single detector and/or other suitable focusing and detection configurations may be used.

Signal analyzer 34 typically comprises, in part, an energy-dispersive pulse processor, as is known in the art. Typically, the signal analyzer is configured as a multi-channel analyzer (MCA), which counts the fluorescent photons as a function of photon energy. A digital processor 36 computes the intensity spectrum of the X-ray photons captured by the detectors based on the counts output by signal analyzer 34. Alternatively, detectors 32 and signal analyzer 34 may be configured as a wavelength-dispersive detection and processing system. Processor 36 typically comprises a general-purpose computer, which performs the digital processing functions of system 20 under the control of suitable software. The software may be downloaded to the processor in electronic form, over a network, for example, or it may alternatively be provided on tangible, non-transitory media, such as optical, magnetic or electronic memory media.

Typically, wafer 22 is mounted on a movable platform, such as a motion stage 23, so as to enable the wafer to be translated and/or rotated with respect to X-ray beam 26 and detectors 32. Alternatively, the wafer may be mounted on a suitable stationary fixture while tube 24, optics 28 and detectors 32 are moved, so that the X-ray beam can be directed at different locations on the wafer. Processor 36 is typically coupled to control motion stage 23 and other elements of system 20, either on instructions of a system operator or automatically, in accordance with pre-programmed calibration and test recipes.

System 20 may be further configured to capture and process X-rays scattered from wafer 22 by other mechanisms, such as reflection, diffraction, and/or small-angle scattering. Multi-function systems of this sort are described, for example, in U.S. Pat. Nos. 6,381,303 and 6,895,075 and 7,551,719, whose disclosures are incorporated herein by reference.

Figure 2:
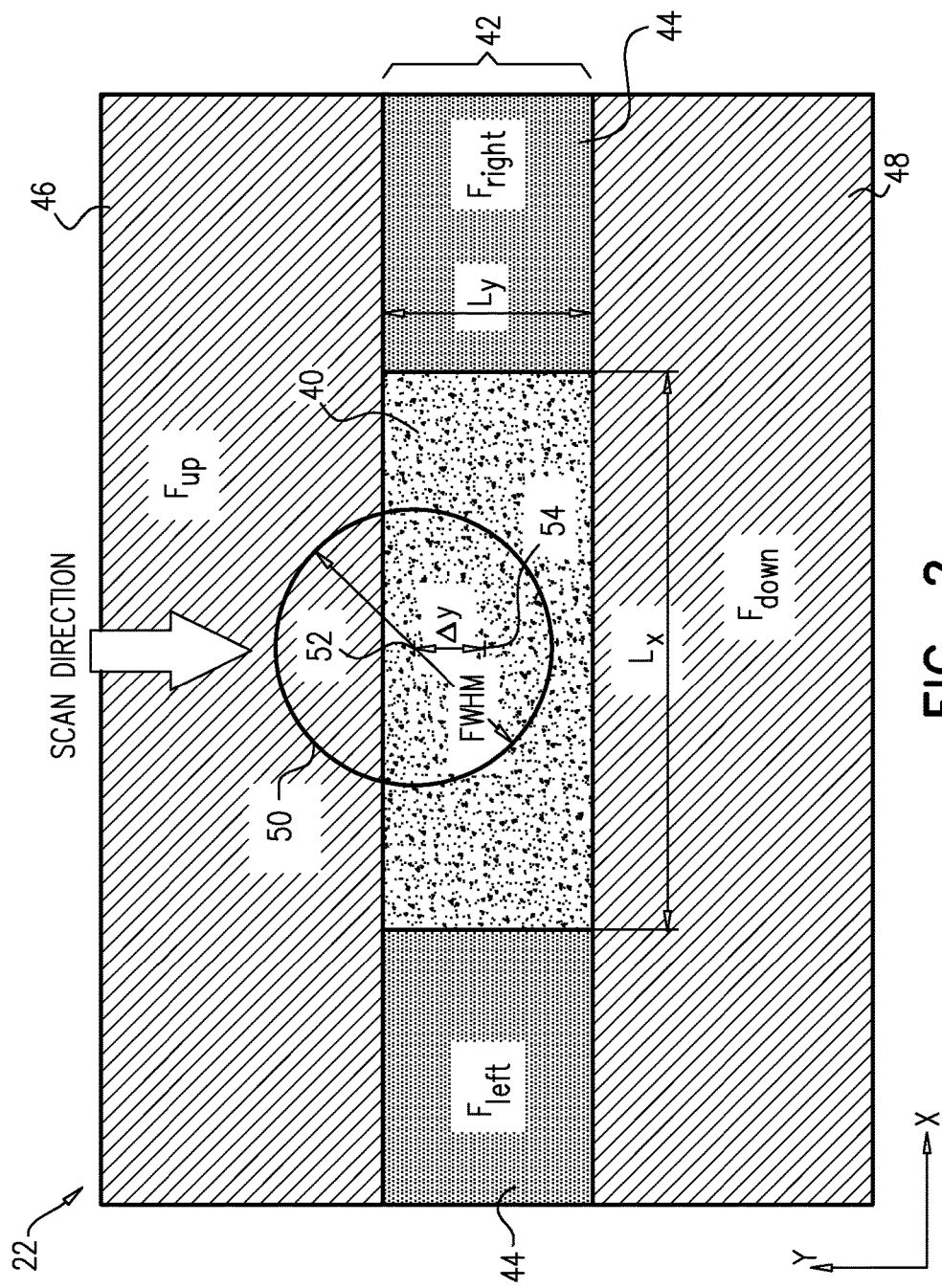
FIG. 2 is a schematic top view of a region on a semiconductor wafer showing parameters of an X-ray beam scan over a pad of interest (POI) on the wafer, in accordance with an embodiment of the invention.

FIG. 2 is a schematic top view of semiconductor wafer 22 showing parameters of a calibration scan of an X-ray beam 50 over a pad of interest (POI) 40 on the wafer, in accordance with an embodiment of the invention. In this example, POI 40 is a rectangular metal pad, of dimensions $L_X \times L_Y$, which is located in a scribe line 42 between dies 46 and 48 of wafer 22. Scribe line 42 contains neighboring features 44. Dies 46 and 48 are depicted in FIG. 2 as homogeneous areas, but in actuality typically contain features of sizes considerably smaller than beam 50.

In the derivation that follows, it is assumed, for the sake of simplicity, that $L_X$ is large enough (as is often the case) so that beam 50 can be focused onto POI 40 without overlap onto features 44. At the same time, it is assumed that the features adjacent to POI 40 in dies 46 and 48 are small enough so that the XRF spectra emitted from the dies are averaged over these features and do not change with the position of beam 40. POI 40 is treated, in effect, as a linear feature of infinite length in the X-direction, bordered by infinite, homogeneous regions on either side in the Y-direction. Alternatively, the principles of the derivation that follows may be applied, mutatis mutandis, to rectangular pads that are smaller than beam 50 in both X- and Y-directions, as well as pads of other shapes, such as circular and elliptical pads.

In a calibration phase of system 20, processor 36 causes beam 50 to scan across POI 50, as illustrated by the arrow in FIG. 2, and measures the resulting XRF in each scan location. Beam 50 is assumed to have a Gaussian profile, with a certain full width at half-maximum amplitude (FWHM), as represented by the circle representing the beam in the figure. The Gaussian beam has wide tails that extend far beyond the FWHM, as is known in the art. The distance of a center 52 of beam 50 from a center 54 of POI 50 is represented as $\Delta y$ and is advanced in small steps, for example steps of 10 µm, while processor 36 measures and records the XRF intensity in an emission line or lines of interest at each step.

In the beam location pictured in FIG. 2, detectors 32 will receive XRF emitted from both POI 40 and die 46, with the relative contributions changing in the course of the scan. These contributions, per unit area, are represented in terms of effective thicknesses: $F_{CENTER}$ for POI 40, and $F_{LEFT}$, $F_{RIGHT}$, $F_{UP}$ and $F_{DOWN}$ for features 44 and dies 46 and 48, respectively. The effective thicknesses correspond to the actual, physical thickness of the layers on wafer 22 in each location, weighted by the relative concentration in each area of the element that is responsible for the XRF emission line of interest.

Figure 3:
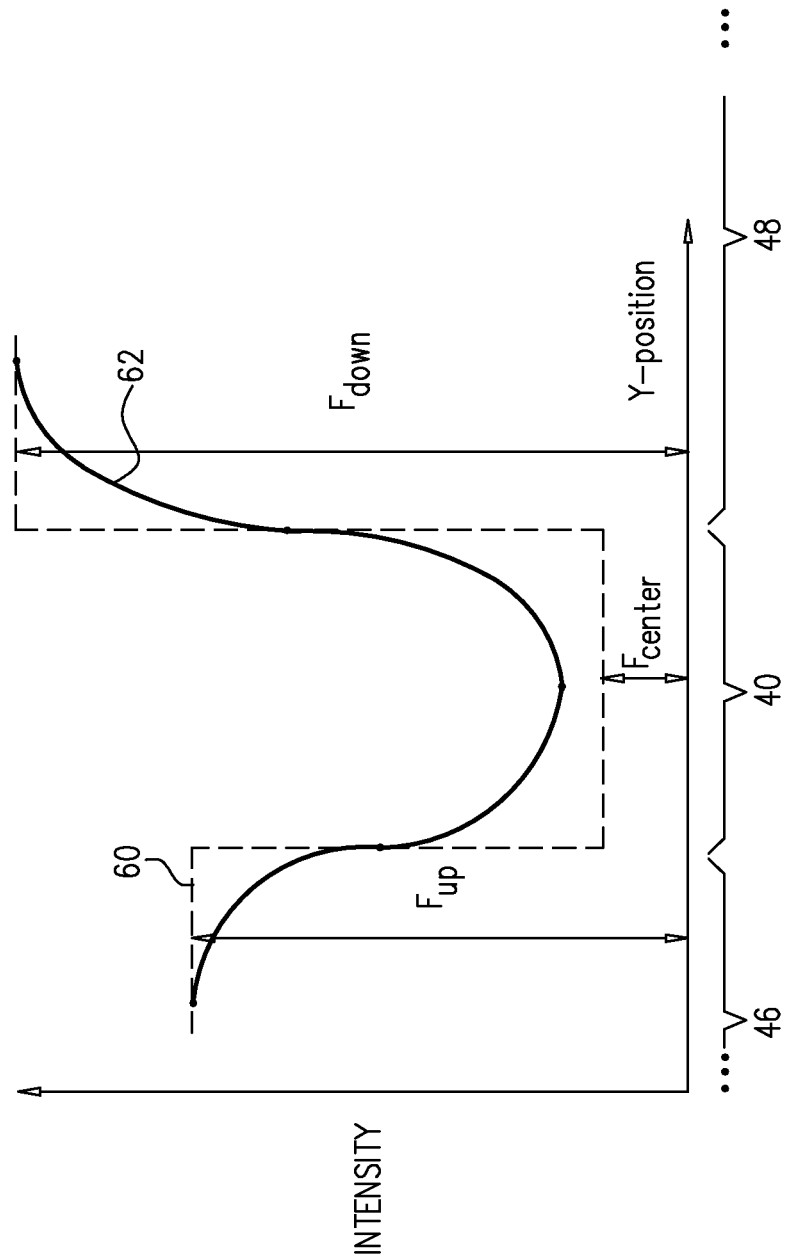
FIG. 3 is a schematic plot of X-ray fluorescence (XRF) intensity as a function of position of the exciting X-ray beam during a scan over a POI on the wafer, in accordance with an embodiment of the invention.

FIG. 3 is a schematic plot of XRF intensity as a function of position of X-ray beam 50 during the scan over POI 40 that is illustrated in FIG. 2, in accordance with an embodiment of the invention. A dashed line 60 represents the effective thickness for a given element, while a solid line 62 represents the emitted intensity in a certain XRF emission line of the given element, as measured in the course of a scan. At each Y-location within the scan, the measured XRF intensity will correspond to a sum of emissions from the areas irradiated by beam 50 at that location.

In this example, there is a substantially greater amount of the element giving rise to the emission line of interest in dies 46 and 48 than in POI 40, and the effective thickness $F_{CENTER}$ is therefore considerably less than $F_{UP}$ or $F_{DOWN}$. Consequently, even when beam 50 is perfectly aligned on POI 40, the background areas above and below the POI will make substantial contributions to the measured XRF signal. The embodiments described herein enable processor 36 to compensate for these background contributions and thus extract a measured XRF value that represents only the contribution of the material in POI 40. A normalized thickness factor F for the background areas, which is extracted during the calibration phase, is taken to be an average of the effective thicknesses of the background areas relative to the POI, i.e., in the present example:

$$F = (F_{UP} + F_{DOWN})/2F_{CENTER}.$$

Different elements in POI 40 and the surrounding environment on wafer 22 will have different effective thicknesses and corresponding intensity curves in their emission lines. Therefore, in contrast to the situation shown in FIG. 3, a given test recipe will generally (although not necessarily) involve measurement of at least one XRF emission line for which $F_{CENTER}$ and the corresponding XRF intensity of curve 62 are substantially greater for scan locations covering the POI than for peripheral scan locations in dies 46 and 48.

Figure 4:
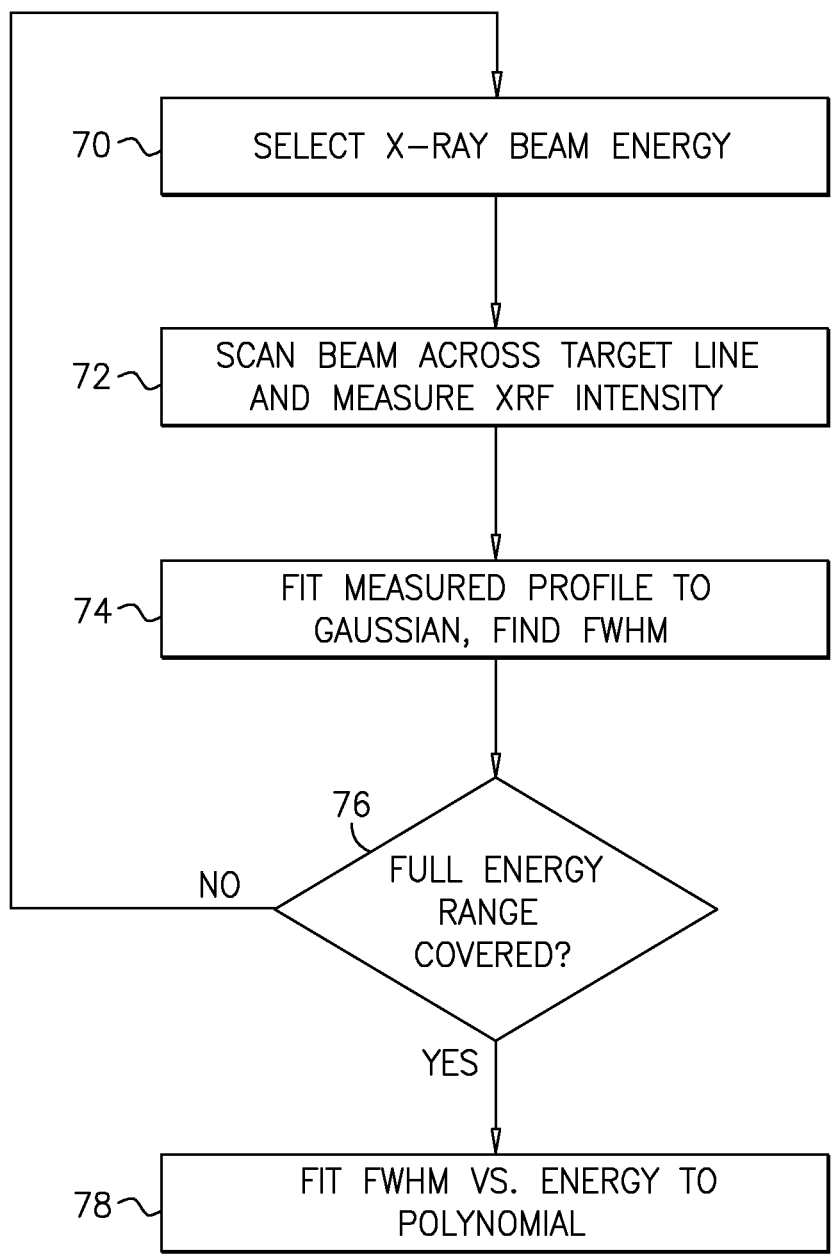
FIG. 4 is a flow chart that schematically illustrates a method for calibrating X-ray beam size, in accordance with an embodiment of the invention.

FIG. 4 is a flow chart that schematically illustrates a method for calibrating the size of X-ray beam 50, in accordance with an embodiment of the invention. This procedure is generally performed, either automatically by processor 36 or under operator control, following the initial setup and alignment of system 20. The purpose of the procedure is to accurately measure the beam profile (and specifically the FWHM) of X-ray beam 50 at a range of energies spanning the energy range of X-ray excitation that will be used for analysis, for example, 1-40 keV. The procedure is typically repeated after significant maintenance and modifications, such as replacement of X-ray tube 24 or optics 28. Performing this sort of beam calibration procedure on two different XRF measurement systems makes it possible to take recipes that were developed and calibrated on one of the systems and use them on the other, without recalibrating the entire recipe.

The method of FIG. 4 begins with selection of an X-ray beam energy, at an energy setting step 70. Once X-ray tube 24 has been set to operate at the selected energy, the beam is scanned across a linear target, such as a suitable metal wire or edge, at a scanning step 72. Detectors 32 measure XRF emission from the target line in a characteristic emission line of the metal. The intensity of this XRF emission will be proportional to the integrated intensity of the part of the X-ray beam that strikes the target in any given scan location. To extract the actual beam profile from the scan measurements, processor 36 fits the measured profile of XRF intensity to a parametric model of the intensity expected for a Gaussian beam convolved with an appropriate shape function for the metal feature, such as a top-hat in the case of a wire or a Heaviside function in the case of as edge, at a fitting step 74. The fitting process typically uses non-linear regression and results in a value of the FWHM for the current beam energy.

The procedure of steps 70, 72 and 74 is repeated for a number of different X-ray beam energies, until the entire energy range of interest has been covered, at a measurement completion step 76. It is not necessary that the measurements actually be performed at all energies of interest within the range. Instead, processor 36 fits the measurements of FWHM against energy (E) to a model function, such as a quadratic or other polynomial, at a modeling step 78. Typically, the dependence of beam width on energy is monotonic, with the FWHM decreasing as energy increases (for example, from 25 μm at 10 keV to 15 μm at 30 keV). Therefore, a quadratic will give a good estimate of the actual beam width and will allow the FWHM to be computed from the model at intermediate energy values. The quadratic expression contains fit parameters w0, w1 and w2 and has the general form:

$$FWHM(E)=w0+w1E+w2E^2.$$

Figure 5:
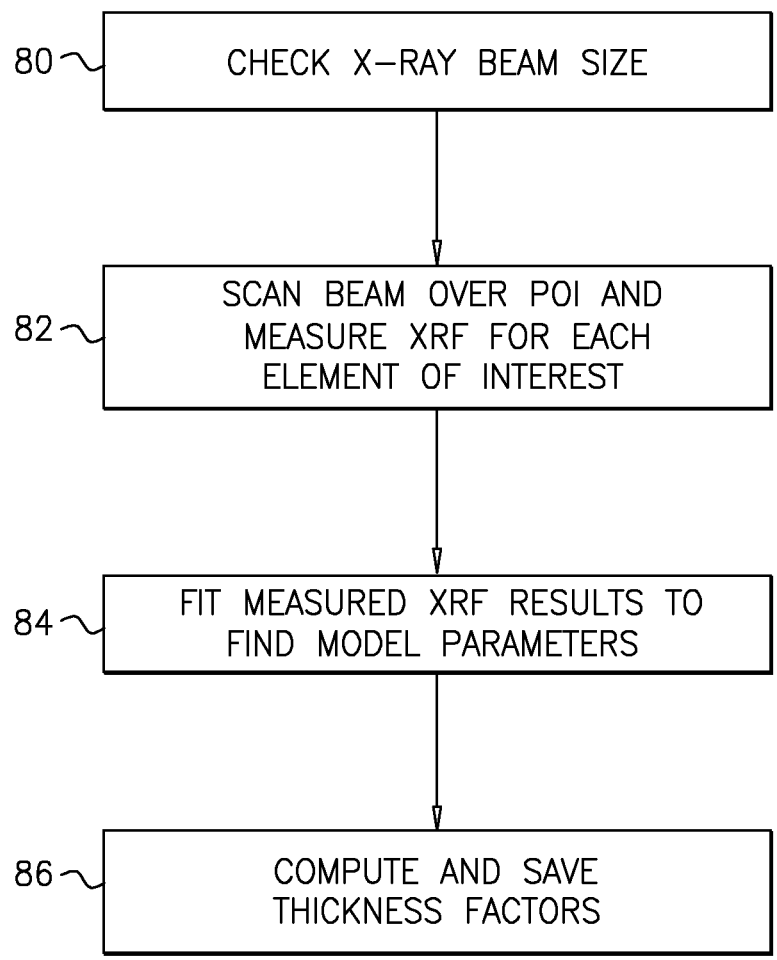
FIG. 5 is a flow chart that schematically illustrates a method for computing relative emission factors for use in analysis of XRF measurements, in accordance with an embodiment of the invention.

FIG. 5 is a flow chart that schematically illustrates a method for computing relative emission factors (referred to herein as thickness factors) for use in analysis of XRF measurements, in accordance with an embodiment of the invention. These relative emission factors are referred to herein as (normalized) thickness factors, as defined above, represented by the symbol F. Again, the method of FIG. 5 may be carried out automatically by processor 36 and/or manually under operator control. The method is typically performed once for each element or emission line of interest in a given POI, meaning that multiple thickness factors may be derived for the POI, corresponding respectively to the different elements.

An appropriate X-ray beam energy is selected to excite the element of interest, and the X-ray beam size (FWHM) is determined for the given energy, at a beam size checking step 80. The beam size is typically derived from the model that was extracted previously, as described above, but it may alternatively be calibrated directly if and when needed. Processor 36 scans X-ray beam 50 over POI 40, and measures the intensity of XRF emission received by detectors 32, at a beam scanning step 82. Typically, the measurement is made over a range that is two to three times the width ($L_Y$) of POI 40, with measurements made at increments in Δy that are 10-20% of the beam width. In the example shown in FIG. 2, it is necessary to scan only in the Y-direction, but in other geometries, the beam may be scanned over the POI in both X- and Y-directions.

For each element of interest in POI 40, processor 36 fits the measured XRF intensity as a function of scan position to a model of the POI and surrounding background areas, typically using nonlinear regression, at a model fitting step 84. The model parameters include the known shape and dimensions of the POI and the X-ray beam width, along with the unknown relative contributions of the POI and background areas. (Alternatively, the size and offset of the POI and/or the FWHM of the X-ray beam can also be treated as variables in the model.) The result of the model fitting performed at step 84 is the normalized average thickness factor F for the element in question in POI 40, as defined above. F can range from zero, when the element is absent from the background areas adjacent to the POI in dies 46 and 48, to values much greater than one, as in the example shown in FIG. 3, occurring, for example, when a thin test pad is surrounded by thicker background areas with high concentrations of the given element.

Processor 36 saves the values of F that are thus derived for the elements in POI 40 for subsequent use in conjunction with test recipes that are applied to the POI, as described below.

Figure 6:
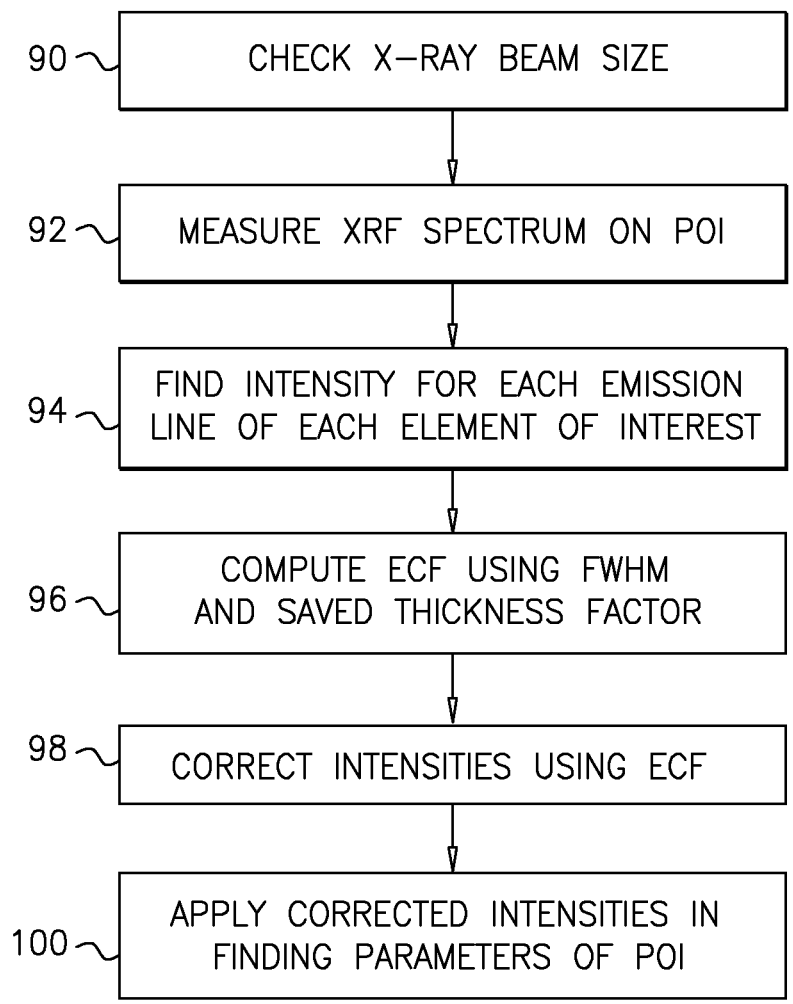
FIG. 6 is a flow chart that schematically illustrates a method for XRF measurement and analysis of a feature on a sample, in accordance with an embodiment of the invention.

FIG. 6 is a flow chart that schematically illustrates a method for XRF measurement and analysis of a feature on a sample, such as POI 40, in accordance with an embodiment of the invention. As an initial step, which will be used in the subsequent analysis, processor 36 determines the FWHM of X-ray beam 50, at a beam size checking step 90. In general, the processor can use the results of the previous beam measurements and model derived in FIG. 4 or a re-measurement made at some intervening time, such as system maintenance. The beam size measurement can be redone automatically or manually at any time between the calibration and test phases. Thus, it is typically not necessary to actually measure the beam size at step 90, unless the recipe is being implemented for the first time on a new tool or there have been recent changes in or adjustments to X-ray tube 24 or optics 28. In any event, there is no requirement that the profile of the X-ray beam used in the measurements of FIG. 6 be the same as the beam profile used in the calibration procedure of FIG. 5.

Processor 36 operates system 20 to position beam 50 on POI 40 and measure the spectrum of XRF emission, at an XRF acquisition step 92. The processor analyzes the measured emission in order to find the net intensity of each emission line of each element of interest in the spectrum, at an intensity measurement step 94. The "net intensity" is found by subtracting the broadband X-ray background intensity out of the spectrum. (This broadband spectral intensity is distinct from and unrelated to the correction of intensity in specific spectral lines due to the XRF contribution of the background areas surrounding POI 40.)

For each element, processor 36 computes an environmental correction factor (ECF), using the known FWHM and thickness factor F, at an ECF computation step 96. The ECF depends upon and compensates for the fraction of the X-ray beam 50 that is incident on the background areas of dies 46 and 48 surrounding POI 40 on the test wafer. In general terms:

$$ECF^{-1} \equiv \alpha = (\iint_{pad} G(x,y)dxdy + F\iint_{env.} G(x,y)dydy)$$

wherein G(x,y) is a symmetrical Gaussian function with σ=FWHM/2.35. The above expression can be rewritten as the sum of a pad contribution P(w) and a background (environment) contribution E(w), wherein w is the beam width:

$$\alpha = [P(w)+E(w)] = \{P(w)+F[1-P(w)]\}$$

For the specific geometry that is shown in FIG. 2, the pad contribution is given by:

$$P(w) = \int_{-L_x/2}^{L_x/2} \int_{-L_y/2}^{L_y/2} \exp\left[-\frac{(x-x_0)^2 + (y-y_0)^2}{2\sigma^2}\right] dx\,dy$$

Processor 36 applies the ECF values computed for each element of interest in POI 40 in order to correct the measured intensities, at an intensity correction step 98. Specifically, the processor scales the net intensities that were measured at step 94 by multiplication with the corresponding ECF values computed at step 96. This scaling compensates both for the fraction of the intensity of XRF from POI 40 that is lost due to the portion of beam 50 that falls outside the POI and for the contribution of background XRF emission from dies 46 and 48. The scaled intensity closely approximates the emission intensity that would have been obtained if beam 50 were contained entirely within POI 40.

Processor 36 uses the scaled intensities in computing properties of POI 40, such as composition and thickness, at a pad analysis step 100. For this purpose, the processor may apply techniques of quantitative analysis that are known in the art, such as regression equations or fundamental parameters. The resulting properties are, to close approximation, independent of the influence of the wafer environment of the POI.

Figure 7:
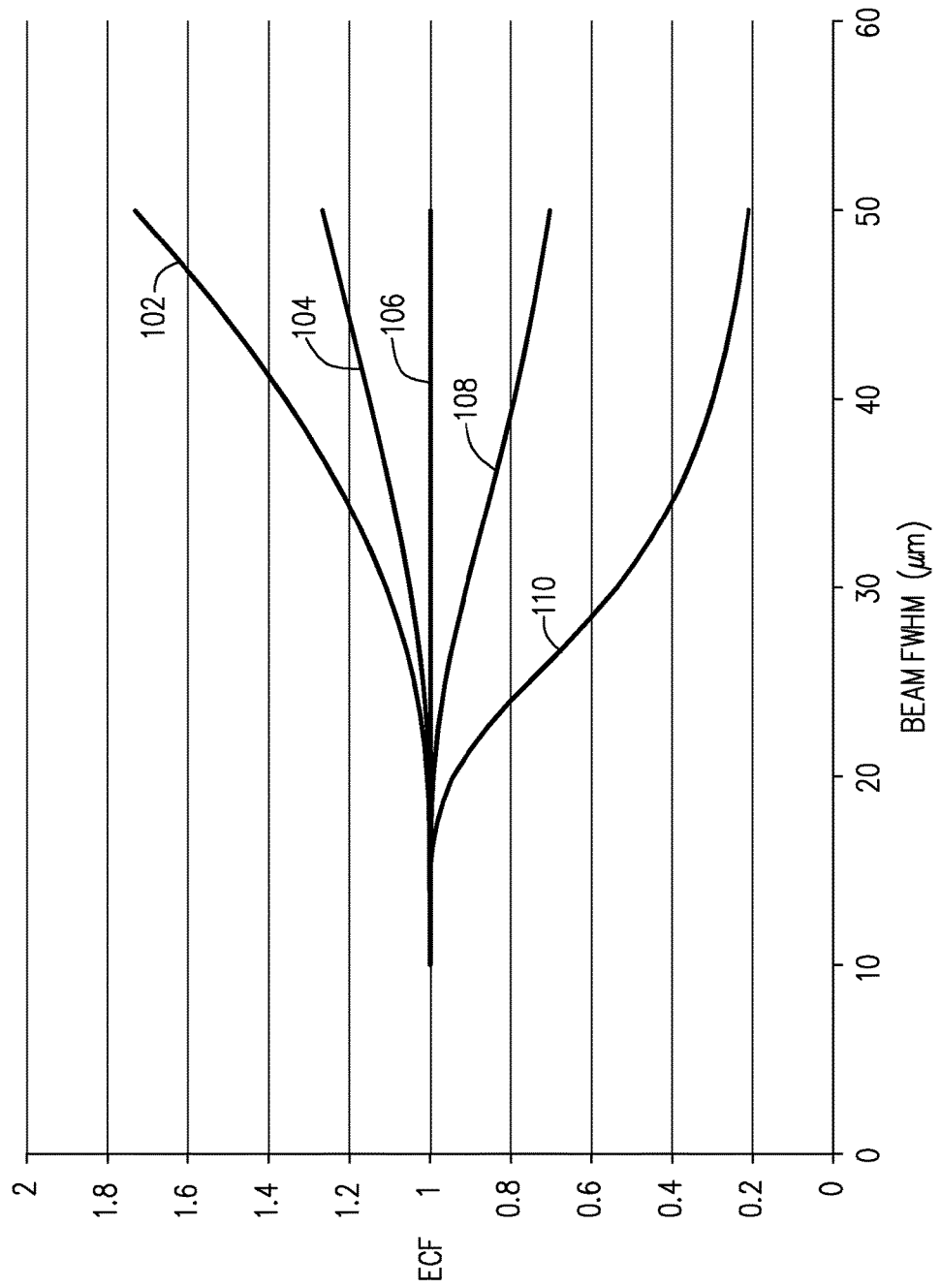
FIG. 7 is a plot that schematically shows environmental correction factors computed for various different test conditions, in accordance with an embodiment of the invention.

FIG. 7 is a plot that schematically shows environmental correction factors computed for various different test conditions, in accordance with an embodiment of the invention. Each of curves 102, 104, 106, 108 and 110 shows the value of ECF as a function of the FWHM of beam 50 for a different, respective value of the thickness factor F, with a test pad of dimensions 50×50 μm. Specifically, the thickness factor has the following values:

Curve 102—F=0
Curve 104—F=0.5
Curve 106—F=1
Curve 108—F=2
Curve 110—F=10.

In curve 102, the background areas make no contribution to the XRF emission intensity, and the ECF therefore scales up the measured intensity to compensate for lost signal due to the portion of the excitation beam that misses the POI. In curves 108 and 110, on the other hand, the measured XRF intensity is scaled down by the ECF to compensate for the strong background XRF intensity.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for X-ray measurement, comprising:
   in a calibration phase, scanning a first X-ray beam, having a first beam profile, across a feature of interest on a calibration sample and measuring first X-ray fluorescence (XRF) emitted, in response to the first X-ray beam, from the feature and from background areas of the calibration sample surrounding the feature;
   computing, responsively to the first XRF and the first beam profile, a relative emission factor indicative of a relation of XRF emission intensities between the feature and the background areas surrounding the feature;
   in a test phase, directing a second X-ray beam, having a second beam profile, different from the first beam profile, to impinge on the feature of interest on a test sample and measuring second XRF emitted from the test sample in response to the second X-ray beam; and
   computing a property of the feature of interest on the test sample by applying the relative emission factor together with the second beam profile to the measured second XRF.

2. The method according to claim 1, wherein the computed property is selected from a group of properties consisting of a composition and a thickness of the feature.

3. The method according to claim 2, wherein computing the property comprises:
   computing, based upon the relative emission factor and the second beam profile, an environmental correction factor;
   calculating a corrected intensity of the second XRF by scaling a measured intensity of the second XRF by the environmental correction factor; and
   deriving the computed composition or thickness from the corrected intensity.

4. The method according to claim 3, wherein the environmental correction factor depends upon and compensates for a fraction of the second X-ray beam that is incident on the background areas surrounding the feature of interest on the test sample.

5. The method according to claim 1, wherein computing the relative emission factor comprises measuring the first XRF and computing different, respective relative emission factors for a plurality of different elements in the feature of interest, at different, respective XRF energies, and
   wherein computing the property comprises selecting one or more of the respective relative emission factors to apply depending upon an energy of the measured second XRF.

6. The method according to claim 1, and comprising, in the calibration phase, measuring the first beam profile.

7. The method according to claim 6, wherein measuring the first beam profile comprises measuring a width of the first beam at a plurality of different energies of the first X-ray beam, and finding an energy-dependence of the width, and wherein computing the relative emission factor comprises estimating, based on the energy-dependence, the width of the first beam at a specified energy, and applying the estimated width in finding the relative emission factor.

8. The method according to claim 7, wherein measuring the first beam profile comprises, at each of the different energies, scanning the first X-ray beam across an edge of a target, and measuring an intensity of the XRF from the target while scanning the first X-ray beam.

9. The method according to claim 6, and comprising, in the test phase, measuring the second beam profile, wherein computing the property comprises applying the measured second beam profile, together with the relative emission factor, in computing the property.

10. The method according to claim 1, wherein the calibration and test samples comprise semiconductor wafers, and wherein the feature of interest comprises a metal pad formed in a predefined location on each of the semiconductor wafers, while the background areas contain other structures formed on the semiconductor wafers around the predefined location.

11. Apparatus for X-ray measurement, comprising:
   an X-ray beam source, which is configured to direct an X-ray beam to impinge on a sample;
   an X-ray detector, which is configured to sense X-ray fluorescence (XRF) emitted from the sample in response to the X-ray beam;
   a motion assembly, which is configured to cause the X-ray beam to scan across the sample; and
   a processor, which is configured to control the X-ray beam source and the motion assembly and to receive signals from the X-ray detector in response to the emitted XRF in a calibration phase and in a test phase,
   wherein in the calibration phase, the motion assembly scans a first X-ray beam, having a first beam profile, across a feature of interest on a calibration sample and the processor measures first XRF emitted, in response to the first X-ray beam, from the feature and from background areas of the calibration sample surrounding the feature and computes, responsively to the first XRF and the first beam profile, a relative emission factor indicative of a relation of XRF emission intensities between the feature and the background areas surrounding the feature, and
   wherein in the test phase, the X-ray source directs a second X-ray beam, having a second beam profile, different from the first beam profile, to impinge on the feature of interest on a test sample, and the processor measures second XRF emitted from the test sample in response to the second X-ray beam and computes a property of the feature of interest on the test sample by applying the relative emission factor together with the second beam profile to the measured second XRF.

12. The apparatus according to claim 11, wherein the computed property is selected from a group of properties consisting of a composition and a thickness of the feature.

13. The apparatus according to claim 12, wherein the processor computes the property by:
computing, based upon the relative emission factor and the second beam profile, an environmental correction factor;
calculating a corrected intensity of the second XRF by scaling a measured intensity of the second XRF by the environmental correction factor; and
deriving the computed composition or thickness from the corrected intensity.

14. The apparatus according to claim 13, wherein the environmental correction factor depends upon and compensates for a fraction of the second X-ray beam that is incident on the background areas surrounding the feature of interest on the test sample.

15. The apparatus according to claim 11, wherein the processor is configured to measure the first XRF and to compute different, respective relative emission factors for a plurality of different elements in the feature of interest, at different, respective XRF energies, and to select one or more of the respective relative emission factors to apply in computing the property depending upon an energy of the measured second XRF.

16. The apparatus according to claim 11, wherein the processor is configured, in the calibration phase, to measure the first beam profile.

17. The apparatus according to claim 16, wherein the processor is configured to measure a width of the first beam at a plurality of different energies of the first X-ray beam, to find an energy-dependence of the width, and to estimate, based on the energy-dependence, the width of the first beam at a specified energy and apply the estimated width in finding the relative emission factor.

18. The apparatus according to claim 17, wherein the first beam profile is measured by scanning the first X-ray beam, at each of the different energies, across an edge of a target, and measuring an intensity of the XRF from the target while scanning the first X-ray beam.

19. The apparatus according to claim 16, wherein the processor is configured, in the test phase, to measure the second beam profile, and to apply the measured second beam profile, together with the relative emission factor, in computing the property.

20. The apparatus according to claim 11, wherein the calibration and test samples comprise semiconductor wafers, and wherein the feature of interest comprises a metal pad formed in a predefined location on each of the semiconductor wafers, while the background areas contain other structures formed on the semiconductor wafers around the predefined location.

* * * * *